United States Patent [19]

Helsley et al.

[11] 4,110,459

[45] Aug. 29, 1978

[54] BENZOYLPIPERIDYLALKYLINDOLES IN ALLEVIATING PAIN

[75] Inventors: Grover C. Helsley, Pottersville; Joseph T. Strupczewski, Flemington; Beth Ann Gardner, Stanhope, all of N.J.

[73] Assignee: American Hoechst Corporation, Bridgewater, N.J.

[21] Appl. No.: 808,513

[22] Filed: Jun. 21, 1977

Related U.S. Application Data

[60] Division of Ser. No. 663,820, Mar. 4, 1976, Pat. No. 4,046,900, which is a continuation-in-part of Ser. No. 594,042, Jul. 8, 1975.

[51] Int. Cl.$^2$ ............................................. A61K 31/445
[52] U.S. Cl. .................................................... 424/267
[58] Field of Search ......................................... 424/267

[56] References Cited

U.S. PATENT DOCUMENTS

| | | | |
|---|---|---|---|
| 3,639,414 | 2/1972 | Archer | 260/295 B |
| 3,686,213 | 8/1972 | Poletto et al. | 260/326.15 |
| 3,850,935 | 7/1974 | Derible et al. | 260/293.61 |

*Primary Examiner*—Stanley J. Friedman
*Attorney, Agent, or Firm*—Curtis, Morris & Safford

[57] ABSTRACT

New benzoylpiperidylalkylindoles and related compounds possessing tranquilizing, anti-hypertensive and analgesic properties and a process for the preparation thereof are described.

1 Claim, No Drawings

BENZOYLPIPERIDYLALKYLINDOLES IN ALLEVIATING PAIN

This is a division, of application Ser. No. 663,820, filed Mar. 4, 1976 now U.S. Pat. No. 4,046,900.

Said application is a continuation in part of application Ser. No. 594,042, filed July 8, 1975.

This invention relates to benzoylpiperidylalkylindoles and related compounds possessing tranquilizing properties and to a process for the preparation thereof. Additionally, some compounds of the invention also demonstrate antihypertensive and analgesic properties.

To the best of our knowledge, the compounds of the present invention have not heretofore been described. Indoles exhibiting action on the cardiovascular system are mentioned in U.s. Pat. No. 3,527,761 (1970). U.S. Pat. Nos. 3,188,313 (1965) and 3,217,011 (1965) describe 1-[1,2 and 3-indolyl]-lower piperazine derivatives and 1-(indolylglyoxalyl)piperidines, respectively as having important biological activity. Additionally, U.S. Pat. No. 3,821,387 (1974) describes 3-(omega-substituted alkyl)-indoles as being useful in the treatment of Parkinsonism. However, the compounds of the present invention have substantial structural differences with respect to the prior art.

The compounds of the invention conform to the general formula

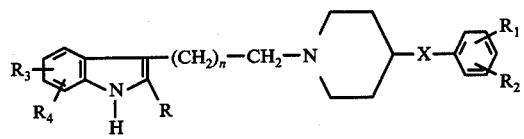

wherein X is C=O or CHOH; R is hydrogen or methyl; $R_1$ and $R_2$ are the same or different and stand for hydrogen, halogen, straight or branched chain alkyl of up to 5 carbon atoms, alkoxy of up to 5 carbon atoms, trifluoromethyl, hydroxy, phenyoxy or phenyl; $R_3$ and $R_4$ are hydrogen or methoxy; n is the integer 2 or 2; and the acid addition salts thereof prepared from pharmaceutically acceptable acids.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The compounds of the invention are prepared by either of the two sequences of reactions described below wherein R, $R_1$, $R_2$, $R_3$ and $R_4$ are as defined earlier. The starting compounds, the 4-benzoyl-piperidines, are prepared from N-acetylisonipecotic acid or from 1-acetylisonipecotamide by the methods described by Robert L. Duncan, Jr. et al., J. Med. Chem. 1, 1, (1970).

The 4-(hydroxybenzoyl)piperidines are prepared by a somewhat different method. The N-acetylisonipecotic acid chloride is reacted with an alkoxy substituted benzene under Friedel-Crafts condition to give a 1-acetyl-4-(alkoxybenzoyl)-piperidine. The reaction of this piperidine with hydrogen bromide produces hydrolysis of the acetyl group and dealkylation of the alkoxy group, giving a corresponding 4-(hydroxybenzoyl)piperidine.

Additionally, a benzoylpiperidine can be prepared by the three step method outlined below.

1. A 4-benzoyl-1-methylpiperidine is produced by the reaction of a benzonitrile of the formula

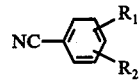

with a Grignard reagent prepared from N-methyl-4-chloropiperidine at a temperature of from 15° C. to the boiling point of the solvent, if any, for from 1 to 15 hours. One preferred method utilizes tetrahydrofuran as the solvent and allows the mixture to react at reflux for 2 hours and then at ambient temperature overnight.

2. The reaction of an above piperidine with a substituted chloroformate such as phenylchloroformate or an alkylchloroformate in the presence of an organic solvent such as methylene chloride or toluene at a temperature of from ambient to the boiling point of the solvent for from a few minutes to 12 hours produces N-carbonyl compound of the formula

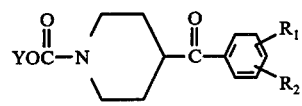

wherein Y is phenyl or alkyl. A preferred chloroformate is phenylchloroformate.

3. A benzoylpiperidine is prepared by cleaving the carbonyl moiety from the above N-carbonyl compound. A preferred method of cleaving is carried out by dissolving an N-carbonyl compound in an aqueous solution of 30–50% potassium hydroxide and an organic solvent such as ethanol and permitting the solution to react at a temperature of from ambient to the boiling point of the solvent for from 1 hour to 60 hours.

METHOD I

A. A sample of 3-(2-bromoethyl)indole is reacted with a 4-benzoylpiperidine of the formula

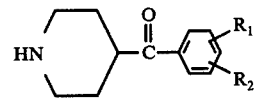

in the presence of a suitable organic solvent such as dimethylformamide, n-butanol, or dimethylsulfoxide, with or without an acid scavenger such as potassium carbonate, triethylamine or sodium bicarbonate, at a temperature of from about 20° C. to the boiling point of the solvent for from 30 minutes to 120 hours to give a compound of the invention of the formula

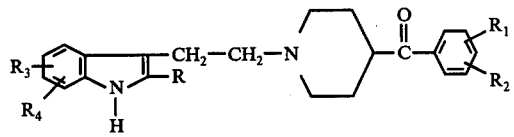

B. These benzoylpiperidylethylindoles can be reduced to give a compound of the invention of the formula

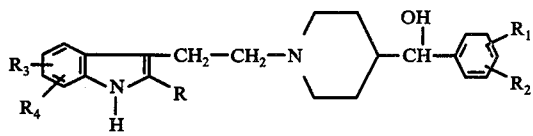

In one preferred method, sodium borohydride is utilized as the reducing agent.

METHOD II

A. A sample of an indole of the formula

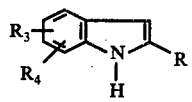

in a solvent such as anhydrous ether is allowed to react with oxalyl chloride at a temperature of from −15 to 15° C. for from a couple of minutes to 1 hour to produce a mixture of a corresponding 3-indoleglyoxyloyl chloride in the solvent which is then added to a cooled solution of 4-benzoylpiperidine in a suitable organic solvent such as chloroform optionally containing an acid scavenger such as potassium carbonate and allowing the mixture to react at a temperature of from 15° to 40° C. for a few minutes to 12 hours to produce a 4-benzoyl-1(indol-3-ylglyoxyloyl)piperidine of the formula

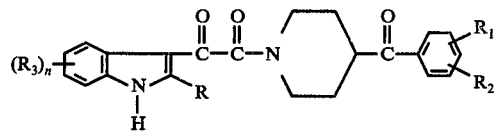

B. An above (indol-3-ylglyoxyloyl)piperidine is reduced to produce an arylhydroxymethylpiperidyle-thylindole a compound of the invention of the formula illustrated in Method I, step B. A preferred method utilized lithium aluminum hydride as the reducing agent, tetrahydrofuran as a solvent, the boiling point of the solvent as the reaction temperature and a reaction time of from a few minutes to 5 hours.

The compounds of the invention are useful as tranquilizers due to their depressant action on the central nervous system of mammals. This acitvity is demonstrated in the mouse observation procedure, a standard assay for central nervous system depressants [Psychopharmacologia, 9, 259 (1966)]. Thus, for example, the minumum effective dose (MED) at which 3-{2-[4-(4-fluorobenzoyl)piperidyl]-ethyl}indole hydrochloride displays significant effects on behavior and reflux depression together with muscle relaxation is 10 mg/kg of body weight. Similarly, MED's of other compounds are:

| Compound | MED mg/kg |
|---|---|
| 3-[2-(4-benzoylpiperidyl)ethyl]indole | 20 |
| 3-{2-[4-(4-toluyl)piperidyl]ethyl{indole | 40 |

Some compounds of the invention are also useful as anti-hypertensive agents due to their ability to depress blood pressure in mammals. Anti-hypertensive activity is measured in the spontaneous hypertensive rate by the indirect tail cuff method described in A. Schwartz, Ed., Methods in Pharmacology, Vol. I, page 135, Appleton-Century-Crofts, New York, New York 1971. In this procedure a group of five animals are dosed orally with 100 mg of the compound per kg. of body weight in relation to a control group of the same number. The antihypertensive activity in this test of some of the compounds of the invention is illustrated in Table I.

TABLE I

| Compound | Day 1 mmHg | Day 3 mmHg |
|---|---|---|
| 3-[2-(4-benzoylpiperidyl)ethyl]indole | −53.8 | −79.7 |
| 3-{2-[4-(4-toluyl)piperidyl]ethyl}indole | −63.6 | −61.0 |
| 3-{2-[4-(4-chlorobenzoyl)piperidyl]ethyl}indole | −39.0 | −67.8 |
| 3-{2-[4-(4-bromobenzoyl)piperidyl]ethyl}indole | −15.8 | −57.2 |

Compounds of the invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 79 (1975)]. For example at doses of 11, 15, 20 and 35 mg/kg of body weight, 3-{2-[4-(4-toluyl)-piperidyl]ethyl}indole, 3-{2-[4-(4-fluorobenzoyl)-piperidyl]ethyl}indole hydrochloride, 3-[2-(4-benzoyl-piperidyl)ethyl]indole, and 3-{2-[4-(4-chlorobenzoyl)-piperidine]ethyl}indole, respectively, exhibit an appoximately 505 inhibition of writhing.

The above data illustrates that the compounds of the present invention are useful as tranquilizers and for the treatment of hypertension and alleviation of pain when administered to mammals at doses of from 0.1 to 100 mg/kg. Examples of the compounds of the invention are;

3-{2-[4-(4-hydroxybenzoyl)piperidyl]ethyl}indole;

3-{2-[4-(4-ethylbenzoyl)piperidyl]ethyl}indole;

3-{2-[4-(4-n-butylbenzoyl)piperidyl]ethyl}indole;

3-{2-[4-(4-ethoxybenzoyl)piperidyl]ethyl}indole;

3-{2-[4-(4-trifluoromethylbenzoyl)piperidyl]ethyl}indole;

3-{2-[4-(2-bromo-4-ethylbenzoyl)piperidyl]ethyl}indole;

3-{2-[4-(3,4-dichlorobenzoyl)piperidyl]ethyl}indole;

3-{2-[4-(4-chlorophenylhydroxymethyl)piperidyl]ethyl}indole; and

3-{2-[4-(4-isopropylphenylhydroxymethyl)piperidyl]ethyl}indole.

The compounds of the resent invention may be administered to a patient by a convenient route such as orally, intramuscularly, intraveneously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active in such compositions is such that a suitable dosage will be obtained. Preferred compositions and preparations according to the present invention are prepared so that an oral dosage unit form contains between 1 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such a s a fatty oil. Other dosage unit forms may contain other various materials which modify the physical form of the dosage unit, for example, as coatings. Thus, tablets or pills may be coated with sugar, shellac, or both. a syrup may contain, in addition to the active compounds sucrose as a sweetening agent, and certain preservatives, dyes and colorings, and flavors. Materials used in preparing these various compositins must be pharmaceutically pure and non-toxic in the amounts utilized.

For the purpose of parenteral therapeutics administration, the active compounds of the invention may be incorporated into a solution of suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other sythetic solvents; anitbacterial agents such as benzyl alcohol or methyl parabens; antioxidants such as ascorbic acid or sodium bisulfite; chelating aagents such as ethylenediaminetetraacetic acid; buffers such as acetates, citrates or phosphates and agents for the adjustment of tonicity such as sodium chloride or dextrose. The parenteral preparation can be enclosed in ampules, dispasable syringes or multiple dose vials made of glass or plastic.

The invention is further illustrated by the folowing examples, given for illustrative purposes.

EXAMPLE I

A. A solution of 51.6 g of isonipecotic acid in 200 ml of acetic anhydride is refluxed for 2 hours and allowed to stir at ambient temperature for 16 hours. The solution is concentrated and the resulting residue is triturated in ether. The solid is collected by filtration and recrystallized from an isopropyl alcohol-diisopropyl ether mixture giving 1-acetylisonipecotic acid as a white solid.

B. A sample of 65.4 g of 1-acetylisonipecotic acid is dissolved in 400 ml of thionyl chloride. The acid chloride precipitates from solution and one liter of petroleum ether is added. The mixture is filtered, the solid residue is washed several times with petroleum ether and dried, giving 1-acetylisonipecotoyl chloride as a white solid.

C. 70 g of 1-acetylisonipecotoyl chloride are slowly added to a stirring mixture of 93.0 g of aluminum chloride in 150 ml of fluorobenzene. After total addition, the mixture is refluxed for one hour. The mixture is poured onto ice and the two resulting layers separate. The aqueous layer is extracted twice with chloroform and the extracts are added to the fluorobenzene which separated previously. The organic solution is dried and concentrated under reduced pressure leaving a crystalline white solid. The solid is recrystallized from a ligroindiisopropyl ether mixture, producing 1-acetyl-4-(4-fluorobenzoyl)piperidine.

D. A solution of 70.6 g of 1-acetyl-4-(4-fluorobenzoyl)piperidine in 200 ml of 6N HCl is refluxed for 2 hours. The cooled solution is extracted twice withether, the aqueous solution basified with sodium hydroxide and then extracted with benzene. The benzene extracts are dried, filtered and the filtrate is concentrated under reduced pressure. The residual oil is dissolved in ether and HCl gas is bubbled into the solution with stirring. The salt is collected by filtration, washed with ether and dried. The salt is recrystallized from isopropanol to give the solid product of 4-(4-fluorobenzoyl)piperidine hydrochloride, mp 222°–224° C.

E. A stirred mixture of 10.1 g of 3-(2-bromoethyl)indole, 15.2 g of 4-(4-fluorobenzoyl)piperidine, and 15.0 g of anhydrous potassium carbonate in 150 ml of n-butanol is refluxed under nitrogen for three hours. The mixture is cooled, filtered, and ether is slowly added to the filtrate to precipitate a white solid, the starting piperidine, which is removed by filtration. The solvent is removed under reduced pressure, leaving a soft orange solid. The solid is dissolved in absolute ethanol, the solution is cooled, and HCl gas is bubbled into the solution. After standing about 5 minutes, the salt precipitates as off-white needles. The needles are recrystallized from a methanol-ether mixture to give slightly off-white needles, mp 267°–269° C. (dec.) of 3-{2-[4-(4-fluorobenzoyl)piperidyl]ethyl}indole hydrochloride.

Analysis: Calculated for $C_{22}H_{23}FN_2O.HCl$: 68.29%C; 6.25%H; 7.24%N. Found: 68.08%C; 6.49%H; 7.32%N.

By following the manipulative procedure of step E, 3-{2-[4-(3-trifluoromethyl)piperidyl]ethyl}indole is prepared by substituting 4-(3-trifluoromethylbenzoyl)piperidine for 4-(4-fluorobenzoyl)piperidine.

4-(3-trifluoromethylbenzoyl)piperidine is prepared in the following manner: A solution of 102.5 g of 3-bromobenzotrifluoride in 25 ml of ether is added dropwise to a stirring mixture of 11.5 g of magnesium turnings in 300 ml of anhydrous ether to maintain a moderate reflux. After total addition the resulting dark mixture is stirred for 1 hour at ambient temperature. A solution of 60.0 g of 1-acetyl-4-cyanopiperidine in 100 ml of tetrahydrofuran is slowly added to this mixture and the mixture is stirred for 16 hours. An excess of an aqueous solution of ammonium chloride is added and the mixture is heated on a steam bath for 3 hours. The mixture is allowed to cool, extracted with benzene and the combined extracts are dried. The solvent is removed and the residue is dissolved in ethanol and basified with sodium hydroxide. The alkaline solution is refluxed for 3 hours, cooled and extracted with benzene. The combined benzene extracts are dried and the benzene is removed, leaving the oil, 4(3-trifluoromethylbenzoyl)piperidine, which is converted to the hydrochloride, mp. 196°–198° C.

EXAMPLE 2

A suspension of 2.8 g of 3-{2-[4-(4-fluorobenzoyl)piperidyl]ethyl}indole, free base of Example 1(e), in 180 ml of isopropanol is added dropwise to a stirred mixture of 102 g of sodium borohydride in 75 ml of isopropanol at 5° C. After total addition, the mixture is permitted to reach ambient temperature, and is stirred for 4.5 hours. The solution is poured into water, the aqueous solution is extracted with methylene chloride, the organic layer is dried, and the solvent is removed under reduced pressure to give a yellow oil. The oil is stirred vigorously in the resence of hexane, and is crystallized to a white solid. The solid is recrystallized from acetonitrile and then from an ethanol-water mixture to give a white powder, mp 188°-190° C., of 3-{2-[4-(4-fluorophenylhydroxymethyl)piperidyl]ethyl}indole.

Analysis: Calculated for $C_{22}H_{25}FN_2O$: 0: 74,96%; 7.15%H; 7.95%N; 5.39%F. Found: 74.85%C; 7.22%H; 8.02%N; 5.05%F.

EXAMPLE 3

A. By following the manipulative procedures described above in Example 1(c), and (d), 37.4 g of 1-acetylisonipecotoyl chloride, [Example 1(b)] and 40 g of aluminum chloride in 90 ml of chlorobenzene are reacted to produce 4-(4-chlorobenzoyl)piperidine hydrochloride, The salt is recrystallized thrice from an ethanol-ether mixture to give a white product, mp 233°-235° C.

B. A solution of 13.0 g of 4-(4-chlorobenzoyl)-piperidine hydrochloride, 10.7 g of triethylamine and 9.8 g of 3-(2-bromoethyl)indole in 350 ml of dimethylformamide is stirred at ambient temperature for 42 hours. Water is added dropwise to the solution to precipitate a pale yellow solid. The solid is collected, washed with water and dried. The solid is recrystallized from isopropanol to give off-white flakes, mp 174°-176° C., of 3-{2-[4-(4-chlorobenzoyl)piperidyl]ethyl}indole.

Analysis:

Calculated for $C_{22}H_{23}ClN_2O$: 72.01%C; 6.31%H; 7.63%N; 9.66%Cl.

Found: 72.14%C; 6.26%H; 7.51%N; 9.76%Cl.

EXAMPLE 4

A. 32.0 g of 1-acetylisonipecotoyl chloride, Example 1(b) are added portionwise to a stirred mixture of 45.3 g of aluminum chloride, 28.3 g of bromobenzene and 120 ml of ethylene dichloride. The solution is stirred overnight, poured onto ice, the organic phase is collected, and the aqueous layer is extracted with chloroform. The organic solutions are combined, dried, and the solvent is removed under reduced pressure to give a yellow oil which crystallizes to a soft solid. The solid is triturated with ether, collected and dried to give 1-acetyl-4-(4-bromobenzoyl)piperidine.

B. A sample of 30.9 g of 1-acetyl-4-(4-bromobenzoyl)piperidine is refluxed for 6 hours in 6N HCl, cooled, and the resulting insoluble salt is collected. The salt is recrystallized from an ethanol-ether mixture, then from isopropanol to give off-white crystals, mp 225°-227° C., 4-(4-bromobenzoyl)piperidine hydrochloride.

C. A sample of 14.6 g of 4-(4-bromobenzoyl)piperidine hydrochloride is treated according to the manipulative procedure described above in Example 3(b) to produce a yellow solid. The solid is recrystallized from 95% ethanol (charcoal treatment) and then from a toluenecyclohexane mixture to give an off-white solid, mp 178-180° C., 3-{2-[4-(4-bromobenzoyl)piperidyl]ethyl}indole.

Analysis:

Calculated for $C_{22}H_{23}BrN_2O$: 64.23%C; 5.64%H; 6.81%N; 19.43%Br.

Found: 64.08%C; 5.55%H; 6.61%N; 19.34%Br.

EXAMPLE 5

A. By following the manipulative procedures described above in Examples 1(c) and (d), 1-acetylisonipecotoyl chloride, Example 1(b), toluene, and aluminum chloride are reacted to produce 4-(4-toluyl)piperidine hydrochloride. The salt is recrystallized thrice from a methanol-ether mixture (one charcoal treatment) to give colorless needles, mp 275°-277° C., (dec.).

B. By following the manipulative procedure described above in Example 3(b), 11.2g of 4-(4-toluyl)-piperidine, 6.1 g of triethylamine and 11.2 g of 3-(2-bromoethyl)indole are treated to produce a white solid. The solid is recrystallized from 95% ethanol (charcoal treatment) to give white flakes, mp 157.5°-159° C., of 3-{2-[4-(4-toluoyl)piperidyl]-ethyl}indole.

Analysis:

Calculated for $C_{23}H_{26}N_2O$: 79.72%C; 7.56%H; 8.08%N.

Found: 79.69%C; 7.55%H; 8.02%N.

EXAMPLE 6

A. By following the manipulative procedure described above in Example 4(a), 32.0 g of 1-acetylisonipecotoyl chloride, [Example 1(b)]are added to a stirring solution of 30.6 g of diphenylether and 45.3 g of aluminum chloride in 100 ml of ethylene dichloride to produce a yellow oil of 1-acetyl-4-(4-phenoxybenzoyl)-piperidine.

B. A sample of 48.8 g of 1-acetyl-4-(4-phenoxybenzoyl)-piperidine is refluxed for 6 hours in 6N HCl. Upon cooling a white solid precipitates from solution, is collected, washed with water, then acetone, and dried. The filtrate is extracted with ether, the aqueous phase is basified with sodium hydroxide and extracted with benzene. The benzene is dried, and the solvent is removed under reduced pressure to give a solid which is converted to a hydrochloride. The salt is recrystallized from an ethanol-ether mixture to give a white solid, mp 219°-220° C., 4-(4-phenoxybenzoyl)piperidine hydrochloride.

C. A solution of 10.3 g of 3-(2-bromoethyl)indole, 14.5 g 4-(4-phenoxybenzoyl)piperidine hydrochloride and 10 g of triethylamine in 350 ml of dimethylformamide is treated according to the manipulative procedure described above in Example 3(b) to produce a yellow solid. The solid is recrystallized thrice from a benzene-hexane mixture (one charcoal treatment) to give a pale yellow crystalline material, mp 180° C., of 3-{2-[4-(4-phenoxybenzoyl)piperidyl]ethyl}indole.

Analysis:

Calculated for $C_{28}H_{28}N_2O_2$: 79.22%C; 6.65%H; 6.60%N.

Found: 79.07%C; 6.65%H; 6.52%N.

EXAMPLE 7

A. A sample of anisole is treated according to the manipulative procedures described above in Example 1(c) and (d) to produce 4-(4-methoxybenzoyl)piperidine hydrochloride which, when recrystallized from isopropanol, had a mp of 251°-256° C.

B. A solution of 11.4 g of 4-(4-methoxybenzoyl)-piperidine, 10.1 g of 3-(2-bromoethyl)indole and 5.6 g of triethylamine in 500 ml of dimethylformamide is treated according to the manipulative procedure described above in Example 3(b) to produce a white solid. The solid is recrystallized twice from 95% ethanol (one charcoal treatment) to give silver-white flakes, mp 175°–177° C., of 3-{2-[4-(4-methoxybenzoyl)piperidyl]ethyl}indole.

Analysis:

Calculated for $C_{23}H_{26}N_2O_2$: 76.20%C; 7.23%H; 7.73%N.

Found: 76.27%C; 7.32%H; 7.83%N.

EXAMPLE 8

A. A sample of 18.0 g of 1-acetyl-4-(4-methoxybenzoyl)piperidine, the intermediate of Example 7(a), is refluxed with 300 ml of 48% of hydrogen bromide under nitrogen for 4 hours. The solution is permitted to stand for 16 hours at 5° C., causing a white solid to precipitate. The solid is collected, washed well with acetone and dried. Recrystallization from methanol gives colorless needles, mp 273°–275° C., of 4-(4-hydroxybenzoyl)-piperidine hydrobromide.

B. A mixture of 9.7 g of 4-(4-hydroxybenzoyl)-piperidine hydrobromide, 6.4 g of sodium bicarbonate and 7.0 g of 3-(2-bromoethyl)indole in 90 ml of dimethylsulfoxide is stirred overnight under nitrogen at 50° C. After cooling to ambient temperature, water is added dropwise, precipitating a gummy brown solid. The supernatant solution is decanted from the solid, triturated with water, collected, and dried. Recrystallization from an ethanol-water mixture gives an off-white solid, mp 212°–214° C. (dec.) of 3-{2-[4-(4-hydroxybenzoyl)-piperidyl]ethyl}indole.

Analysis:

Calculated for $C_{22}H_{24}N_2O_2$: 75.83%C; 6.94%H; 8.04%N.

Found: 75.61%C; 6.85%H; 7.90%N.

EXAMPLE 9

A. A sample of benzene is treated according to the manipulative procedures described above in Example 1(c) and (d) to produce 4-(benzoyl)piperidine hydrochloride. The salt is recrystallized from isopropanol to give a mp of 223°–225° C.

B. A solution of 10.4 g of 4-(benzoyl)piperidine, 6.1 g of triethylamine and 11.2 g of 3-(2-bromoethyl)indole in 350 ml of dimethylformamide is stirred at ambient temperature for 16 hours. Water is added dropwise, precipitating an off-white solid. The solid is collected, washed with water and low boiling petroleum ether, and dried. The solid is recrystallized from 95% ethanol to give white flakes, mp [145°–147° C., of 3-]2-(4-benzoylpiperidyl)ethyl]indole.

Analysis:

Calculated for $C_{22}H_{24}N_2O$: 79.48%C; 7.28%H; 8.43%N.

Found: 79.51%C; 7.33%H; 8.49%N.

EXAMPLE 10

A. By following the manipulative procedure described above in Example 4(a), 25 g of 1-acetylisonipecotoyl chloride are added to stirred suspension of 25 g of aluminum chloride and 14 g of m-fluorotoluene in 220 ml of ethylene dichloride to produce the oil, 1-acetyl-4-(2-fluoro-4-methylbenzoyl)piperidine.

B. A sample of 17.1 g of 1-acetyl-4-(2-fluoro-4-methylbenzoyl)piperidine is refluxed in 200 ml of 6N HCl for 24 hours and then stirred for an additional 6 hours at ambient temperature. The solution is extracted with ether, the aqueous layer is basified with 6N NaOH, extracted with benzene, dried and the solvent is removed under reduced pressure, leaving a yellow oil. The oil is added to ethereal hydrogen chloride and the resulting precipitate is collected, washed well with ether and dried. The solid is recrystallized from a methanol-ether mixture to give the final solid product, mp 220°–221° C. of 4-(2-fluoro-4-methylbenzoyl)piperidine hydrochloride.

C. A solution of 15.5 g of 3-(2-bromoethyl)indole, 17.5 g of 4-(2-fluoro-4-methylbenzoyl)piperidine hydrochloride and 19 g of triethylamine in 500 ml of dimethylformamide is stirred at ambient temperature for 64 hours. Water is added dropwise, resulting in a precipitate. The precipitate is collected by filtration, washed well with water and dried. The solid is recrystallized from a methanol-ether mixture and from a benzene-hexane mixture to give off-white flakes, mp 117°–118° C., of 3-{2-[4-(2-fluoro-4-methylbenzoyl)piperidyl]ethyl}·indole.

Analysis:

Calculated for $C_{23}H_{25}FNO_2$: 75.79%C; 6.92%H; 5.21%F; 7.69%N.

Found: 75.96%C; 7.07%H; 5.15%F; 7.57%N.

EXAMPLE 11

A. A sample of o-xylene is treated according to the manipulative procedures described above in Example 1(c) to give 1-acetyl-4-(3,4-dimethylbenzoyl)piperidine.

B. A sample of 21.3 g of 1-acetyl-4-(3,4-dimethylbenzoyl)piperidine is refluxed in 100 ml 95% ethanol and 100 ml 35% potassium hydroxide for 6 hours and then allowed to stir at ambient temperature overnight. The aqueous layer is extracted with benzene, the organic extracts are combined and dried. The solvent is removed under reduced pressure leaving a yellow oil. The oil is dissolved in ether and hydrogen chloride is bubbled into the solution. The resulting solid precipitate is collected, washed well with ether and dried. The solid is recrystallized thrice from an isopropanol-ether mixture to give the salt, mp 258°–259° C., 4-(3,4-dimethylbenzoyl)piperidine hydrochloride.

C. A solution of 9.6 g of 3-(2-bromoethyl)indole. 11.5 g of 4-(3,4-dimethylbenzoyl)piperidine hydrochloride and 10.1 g of triethylamine in 300 ml of dimethylformamide is treated according to the manipulative procedure described in Example 3(b) to give an indole, which is purified on a silica gel column, eluted with a 5% methanol-benzene mixture and recrystallized from an ethanol-water mixture to give the solid, mp 172°–173° C., 3-{2-[4-(3,4-dimethylbenzoyl)piperidyl]ethyl}indole.

Analysis:

Calculated for $C_{24}H_{28}N_2O$: 79.96%C; 7.83%H; 7.77%N.

Found: 79.95%C; 7.90%H; 7.71%N.

EXAMPLE 12

A. 19.1 g of 1-acetylisonipecotoyl chloride, Example 1(b) are added portionwise to a stirring suspension of 13 g of t-butylbenzene and 27 g of aluminum chloride in 175 ml of dichloroethane. The reaction mixture is refluxed for 1 hours, cooled, and poured onto ice. The organic layer is separated and the aqueous layer is extracted with chloroform. The organic layers are combined, dried, and the solvent is removed under reduced pressure leaving the oil, 1-acetyl-4-(4-t-butylbenzoyl)-piperidine.

B. A sample of 27.6 g of 1-acetyl-4-(4-t-butylbenzoyl)-piperidine is refluxed in 100 ml of ethanol and 100 ml of 35% aqueous potassium hydroxide for 6 hours, and then allowed to stir at ambient temperature for 62 hours. The solution is extracted with benzene, the benzene extracts are dried, and the benzene is removed under reduced pressure leaving an oil. The oil is dissolved in ether and hydrogen chloride gas is bubbled into the solution. The resulting beige precipitate is collected and dried. The precipitate is recrystallized from 2-butanone to give the solid, mp 230°-231° C., 4-(4-t-butylbenzoyl)piperidine hydrochloride.

C. A solution of 9.4 g of 3-(2-bromoethyl)indole, 11.7 g of 4-(4-t-butylbenzoyl)piperidine hydrochloride and 9 g of triethylamine in 350 ml of dimethylformamide is treated according to the manipulative procedure described in Example 3(b) to produce a yellow solid. The solid is recrystallized from a methanol-water mixture (charcoal treatment) then twice from a benzene-hexane mixture to give the off-white indole, mp 173°-174° C., 3-{2-[4-(4-t-butylbenzoyl)piperidyl]ethyl}indole.

analysis:
Calculated for $C_{26}H_{32}N_2O$: 80.37%C; 8.30%H; 7.21%N.
Found: 80.15%C; 8.47%H; 7.07%N.

EXAMPLE 13

A. 16.5 g of 1-acetylisonipecotoyl chloride, Example 1(b) are slowly added to a stirring mixture of 60 ml of m-dimethoxybenzene and 20.0 g of aluminum chloride. Stirring is continued for 1 hour at ambient temperature and then for an additional 1 hour at about 100° C. The reaction mixture is allowed to cool to ambient temperature, poured into ice-water, and extracted with chloroform. The combined extracts are dried and the chloroform is removed leaving a yellow oil. The oil is triturated with hexane to effect a white solid which is collected and dried. Recrystallization from ethyl acetate yields colorless needles, mp 138°-140° C., 1-acetyl-4-(2-hydroxy-4-methoxy-benzoyl)piperidine.

Analysis:
Calculated for $C_{15}H_{19}NO_4$: 64.96%C; 6.90%H; 5.05%N.
Found: 65.05%C; 6.98%H; 4.92%N.

B. A sample of 1-acetyl-4-(2-hydroxy-4-methoxybenzoyl)piperidine is treated according to the manipulative procedure described above in Example 1(d) to give 4-(2-hydroxy-4-methoxybenzoyl)piperidine.

C. A mixture of 4.0 g of 4-(2-hydroxy-4-methoxybenzoyl)piperidine, 3.3 g of 3-(2-bromoethyl)indole and 1.4 g of sodium bicarbonate in 60 ml of dimethylsulfoxide is stirred at ambient temperature for 42 hours and at 60° C. for an additional 6 hours. The reaction mixture is allowed to cool to ambient temperature and water is added dropwise to produce a gummy, brown precipitate. the precipitate is collected and triturated ith ethanol to give a white solid which is recrystallized twice from ethanol (one charcoal treamtent) to give silver-white flakes, mp 150°-152° C., 3-{2-[4-(2-hydroxy-4-methoxybenzoyl)piperidyl]ethyl}indole.

Analysis:
Calculated for $C_{23}H_{26}N_2O_3$: 72.99%C; 6.92%H; 7.40%N.
Found: 73.23%C; 6.92%H; 7.32%N.

EXAMPLE 14

A. 18.7 g of 1-acetylisonipecotoyl chloride, Example 1(bare added slowly to a stirred mixture of 40.0 g of m-dimethoxybenzene and 19.2 g of aluminum chloride in 75 ml of carbon disulfide. The reaction mixture is stirred at ambient temperature for an hour, poured into ice-water and extracted with chloroform, the combined extracts are dried and the chloroform is removed, leaving a yellow oil. The oil is triturated with ether to give a white solid, which is recrystallized twice from ethyl acetate to give the pure solid, mp 132°-134° C., 1-acetyl-4-(2,4-dimethoxybenzoyl)piperidine.

Analysis:
Calculated for $C_{16}H_{21}NO_4$: 65.95%C; 7.26%H; 4.80%N.
Found: 65.86%C; 7.30%H; 4.63%N.

B. By following the manipulative procedure described above in Example 1(b), 7.4 g of 1-acetyl-4-(2,4-dimethoxybenzoyl)piperidine in 250 ml of 6N HCl are treated to give a hydrogen chloride salt which is recrystallized once from an ethanol-ether mixture and twice from ethanol to give the compound, mp 198°-200° C., 4-(2,4-dimethoxybenzoyl)piperidine hydrochloride.

Analysis:
Calculated for $C_{14}H_{19}NO_{03}.HCl$: 58.85%C; 7.05%H; 4.9:%N; 12.41%Cl.
Found: 58.97%C; 7.02%H; 5.11%N; 12.54%Cl.

C. To a stirring solution of 8.0 g of 4-(2,4-dimethoxybenzoyl)piperidine hydrochloride and 6 ml of triethylamine in 250 ml of dimethylformamide is added a solution of 6.4 g of 3-(2-bromoethyl)indole in 50 ml of dimethylformamide. The reaction mixture is permitted to stir at ambient temperature for 72 hours and then 500 ml of water is added dropwise and extracted with chloroform. The combined extracts are dried and most of the chloroform removed leaving a dark oil. The oil is subjected to column chromotography on a silica gel column and eluting with a 3% methanol in chloroform solution to give 3-{2-[4-(2,4-dimethoxybenzoyl)piperidyl]ethyl}indole. The indole is recrystallized thrice from an ethanol-water mixture to give the pure indole, mp 110°-112° C.

Analysis:
Calculated for $C_{24}H_{28}N_2O_3$: 73,44%C; 7.19%H; 7.14%N.
Found: 73.42%C; 7.31%H; 7.18%N.

EXAMPLE 15

A. A few drops of ethyl bromide are added to a stirring suspension, under nitrogen, of 3.2 g of magnesium turnings in 10 ml of tetrahydrofuran. After a reaction begins, 17.7 g of N-methyl-4-chloropiperidine in 50 ml of tetrahydrofuran are added dropwise while manintaining a moderate reflux. After total addition, the reaction mixture is heated at reflux for 1 hour and 15.2 g of 3-tolylnitrile in 10 ml of tetrahydrofuran are slowly added. After this addition is complete the reaction mixture is heated at reflux for an additional 2 hours and then permitted to stir at ambient temperature for 16 hours. The reaction mixture is poured into a solution of 35 g of ammonium chloride in 500 ml of ice-water and heated on a steam bath for 3 hours, cooled and extracted with benzene. The combined benzene extracts are dried and most of the benzene is removed, leaving an orange oil. The oil is dissolved in ether and the oxalate salt is prepared by the addition of a solution of anhydrous oxalic acid in isopropanol. The white oxalate salt is recrystallized twice from ethanol to give the product, mp 183°-185° C., 1-methyl-4-(3-toluyl)piperidine oxalate.

Analysis:
Calculated for $C_{14}H_{19}N.(CO_2H)_2$: 62.53%C; 6.89%H; 4.55%N.
Found: 62.32%C; 7.01%H; 4.52%N.

B. 18.8 g of phenylchloroformate are added dropwise to a solution of 21.3 g of 1-methyl-4-(3-toluyl)piperidine, free base of the above, in 100 ml of methylene chloride and the reaction mixture is stirred at ambient temperature for 16 hours and the solvent removed leaving a dark brown semisolid. The semisolid is suspended in 500 ml of 1N hydrogen chloride solution and extracted with ether. Some of the desired material precipitates from the aqueous phase and is collected. The ether extract is dried and the ether removed under reduced pressure to give a brown solid, which is stirred in a 50% methanol- 2% aqueous potassium carbonate solution at ambient temperature for 16 hours. Filtration of the mixture provides more of the desired product. The combined product is recrystallized twice from an ethanol-water mixture to give the compound, 1-phenoxycarbonyl-4-(3-toluyl)piperidine, mp 127°–130° C.

Analysis:

Calculated for $C_{12}H_{21}NO_3$: 74.28%C; 6.54%H; 4.33%N.

Found: 74.35%C; 6.62%H; 4.29%N.

C. A solution of 11.9 g of 1-phenoxylcarbonyl-4-(3-toluyl)piperidine and 75 ml of an aqueous 50% potassium hydroxide solution in 300 ml of ethanol is heated at reflux for 24 hours and then stirred at ambient temperature for an additional 36 hours. 100 ml of water are added, the ethanol is partially removed, the resulting mixture is extracted with ether and the combined ether extracts are extracted with 1N HCl. The aqueous solution is basified with an aqueous sodium hydroxide solution, extracted with ether, the combined ether extracts are dried, and the ether is removed, leaving a dark oil. The oil is dissolved in ether and ethereal hydrogen chloride is added to produce the salt which is collected by filtration, dried and recrystallized thrice from an ethanol-water mixture to give 4-(3-toluyl)piperidine hydrochloride, mp 196°–197° C., Analysis:

Calculated for $C_{13}H_{17}NOHCl$:65.13%C; 7.57%H; 5.83%N; 14.79%Cl.

Found: 64.90%C; 7.59%H; 5.73%N; 14.65%Cl.

D. 4.2 g of potassium carbonate are added to a stirred solution of 3.8 g of 4-(3-toluyl)piperidine hydrochloride in 400 ml of dimethylformamide. The mixture is stirred at ambient temperature for 1 hour and then a solution of 3.4 g of 3-(2-bromoethyl)indole in 100 ml of dimethylformamide is introduced. The resulting mixture is stirred at ambient temperature for 120 hours, filtered and 1.5 1 of water added dropwise to effect a precipitate. The precipitate is collected and recrystallized thrice from ethanol (one charcoal treatment), to give the indole, mp 171°–173° C., 3-{2-[4-(3-toluyl)piperidyl]ethyl}indole.

Analysis:

Calculated for $C_{23}H_{26}N_2O$: 79.93%C; 7.56%H; 8.09%N.

Found: 79.85%C; 7.71%H; 8.17%N.

EXAMPLE 16

A. By following the manipulative procedure outlined in Example 15(a), a sample of 2-fluorobenzonitrile is treated to produce a hydrochloride salt which is recrystallized twice from an ethanol-ether mixture to give off-white crystals, mp 167°–169° C., 4-(2-fluorobenzoyl)-1-methylpiperidine hydrochloride Analysis:

Calculated for $C_{13}H_{16}FNO \cdot HCl$: 60.58%C; 6.65%H; 5.43%N; 7.37%F.

Found: 60.30%C; 6.78%H; 5.43%N; 7.59%F.

B. 47.0 g of phenylchloroformate are added to a stirring solution of 57.5 g of 4-(2-fluorobenzoyl)-1-methyl piperidine in 750 ml of toluene. The reaction mixture is refluxed for 5 hours, cooled to ambient temperature, filtered, and the solvent is removed leaving a light colored oil. Theoil is triturated with hexane to give a crystalline material which is recrystallized twice from an ethanol-water mixture and once from ethanol The oil give the compound, mp 95°–96° C., 1-phenoxycarbonyl-4-(2-fluorobenzoyl)piperidine.

Analysis:

Calculated for $C_{19}H_{18}FNO_3$: 69.71%C; 5.54%H; 4.28%N; 5.81%F.

Found: 69.45%C; 5.67%H; 4.13%N; 6.10%F.

C. A solution of 40.5 g of 1-phenoxycarbonyl-4(2-flurorobenzoyl)piperidine in 500 ml of ethanol and 500 ml of an aqueous 30% potassium hydroxide solution is stirred at a temperature slightly below reflux for 16 hours, allowed to cool to ambient temperature, diluted with water, and the ethanol is partially removed under reduced pressure. The resulting aqueous suspension is extracted with ether, the combined ether extracts are extracted with 1N hydrogen chloride and the aqueous acid solution is basified with an aqueous sodium hydroxide solution. The basic solution is extracted with ether, the combined ether extracts are dried and the ether is removed under reduced pressure leaving a dark oil. The oil is dissolved in a minumum amount of ehtanol and ethereal-hydrogen chloride is added dropwise to effect a precipitate. The precipitate is collected by filtration, dried and recrystallized twice from an ethanolether mixture to give a white solid, mp 185°–187° C., 4°(2-fluorobenzoyl)piperidine hydrochloride.

Analysis:

Calculated for $C_{12}H_{14}FNO \cdot HCl$:59.14%C; 6.20%H; 5.74%N; 7.80%F.

Found: 58.90%C; 6.36%H; 5.50%N; 7.56%F.

D. A solution of 9.1 g of 3-(2-bromoethyl)indole in 100 ml of dimethyl formamide is added to a stirring solution of 11.2 g of 4-(2-fluorobenzoyl)piperidine hydrochloride and 13 g of potassium carbonate in 400 ml of dimethylformamide. The reaction mixture is stirred at ambient temperature for 24 hours, and then 800 ml of water are added dropwise, yielding a dark precipitate. This mixture is again stirred at ambient temperature for 24 hours and filtered to give a yellow crystalline material which is recrystallized thrice from an ehtanol-water mixture to give an off-white crystalline material, mp 106°–108° C. , 3-{2-[4-(2-fluorobenzoyl)piperidyl]-ethyl}indole.

Analysis:

Calculated for $C_{22}H_{23}FN_2$: 0: 75.40%C; 6.62%H; 7.99%N.

Found: 75.41%C; 6.59%H; 8.03%N.

EXAMPLE 17

A solution of 11.8 g of 3-(2-bromoethyl)-2-methylindole, 20.3 g of 4-(4-toluyl)piperidine [Example 5(a)] in 500 ml of dimethylformamide is treated according to the manipulative procedure described in Example 3(b) to give the off-white solid, mp 192°–194° C., 2-methyl-3-{2-[4-(4-toluyl)piperidyl]ethyl}indole from ethanol.

Analysis:

Calculated for $C_{24}H_{28}N_2O$: 79.96%C; 7.83%H; 7.77%N.

Found: 79.82%C; 7.80%H; 7.69%N.

EXAMPLE 18

A. By following the manipulative procedure described in Example 15(a), (b) and (c), 2-tolylnitrile is treated to produce 4-(2-toluyl)piperidine hydrochloride.

B. To a stirring solution of 4.2 g of 4-(2-toluyl)piperidine hydrochloride and 4.0 g of triethylamine in 150 ml of dimethylformamide is added 3.8 g of 3-(2-bromoethyl)indole. The resulting solution is stirred at ambient temperature for 70 hours and stirring is continued while 500 ml of water are added dropwise. An oil apears which is extracted from the solution with chloroform, the combined chloroform extracts are dried and the excess chloroform is removed, leaving an oil which crystallizes upon standing. The solid product is recrystallized from cyclohexane and then twice from an ethanol-water mixture to give flakes, mp 111°–112° C., 3-{2-[4-(2-toluyl)piperidyl]-ethyl}indole.

Analysis:
Calculated for $C_{23}H_{26}N_2O$: 79.73%C; 7.56%H; 8.09%N.
Found: 79.83%C; 7.69%H; 8.14%N.

EXAMPLE 19

A solution of 8.8 g of 3-(2-bromoethyl)-5-methoxy indole in 100 ml of dimethylformamide is added to a stirring mixture of 4-(4-toluyl)piperidine hydrochloride [Example 5(a)] and 10.1 g of potassium carbonate in 400 ml of dimethylformamide and the reaction mixture is stirred at ambient temperature for 80 hours and then at 50° C. for 10 additional hours. It is cooled to ambient temperature, filtered, and 2 liters of water are added dropwise to produce a precipitate. The precipitate is triturated with ether and eluted with a 5% methanol in benzene solution through a silica gel column. The precipitate is recrystallized from an ethanol-water mixture to give off-white crystals, mp 131°–133° C., 5-methoxy-3-{2-[4-(4-toluyl)piperdyl]ethyl}indole.

Analysis:
Calculated for $C_{24}H_{28}N_2O_2$: 76.56%C; 7.50%H; 7.44%N.
Found: 76.36%C; 7.45%H; 7.19%N.

EXAMPLE 20

A. By following the manipulative procedures outlined in Examples 1(a), (b), (c) and (d), a sample of biphenyl is treated to produce 4-(4-phenylbenzoyl)piperidine.

B. A solution of 10.4 g of 4-(4-phenylbenzoyl)-piperidine, 8.8 g of 3-(2-bromoethyl)indole and 4.5 g of triethylamine in 300 ml of dimethylformamide is treated according to the manipulative procedure outlined in Example 3(b) to produce 3-{2-[4-(4-phenylbenzoyl)-piperidyl]-ethyl}indole. The indole is recrystallized twice from an ethanol-water mixture (one charcoal treatment), thrice from a pyridine-water mixture, and twice from an acetone-water mixture to give the product, mp 189°–192° C.

Analysis:
Calculated for $C_{28}H_{28}N_2O$: 82.32%C; 6.91%H; 6.85%N.
Found: 81.90%C; 7.09%H; 6.80%N.

EXAMPLE 21

A. 8.7 g of oxalyl chloride are added dropwise to a stirring solution, cooled to about −10° C., of 12.0 g of 5,6-dimethoxy-2-methylindole in 250 ml of ether. After addition is complete, the mixture is stirred for 10 minutes, producing a bright orange precipitate of 5,6-dimethoxy-2-methyl-3-indole glyoxylyl chloride which is immediately used for the next step.

B. The above ether suspension of 5,6-dimethoxy-2-methyl-3-indoleglyoxylyl chloride is added portionwise to a cooled stirring mixture of 4-benzoylpiperidine [Example 9(a)], 150 ml of water, 150 ml of chloroform and 25 g of potassium carbonate. The mixture is stirred for 16 hours at ambient temperature, the organic layer is separated and the solvent is removed, leaving a brown oil which is triturated with cyclohexane and then stirred for 16 hours with ether. A white solid results which is collected, dried and recrystallized thrice from methanol to give the compound, mp 188°–190° C., 4-benzoyl-1-(5,6-dimethoxy-2-methylindol-3-ylgloyoxyloyl)piperidine.

Analysis:
Calculated for $C_{25}H_{26}N_2O_5$: 69.10%C; 6.03%H; 6.45%N.
Found: 68.98%C; 6.20%H; 6.38%N.

C. A suspension of 20.2 g of 4-benzoyl-1-(5,6-dimethoxy-2-methylindol-3-ylglyoxyloyl)piperidine in 200 ml of tetrahydrofuran is added dropwise to a stirring solution, under nitrogen at reflux, of 9.6 g of lithium aluminum hydride in 210 ml of tetrahydrofuran. Stirring and refluxing is continued for 3 hours, the mixture is cooled in an ice bath and the excess hydride is destroyed with water. The mixture is filtered and the filtrate is concentrated under reduced pressure, leaving an off-white foam which is triturated with cyclohexane to give an off-white powder. The oxalate salt is prepared by dissolving the free base in isopropanol and slowly adding a solution of oxalic acid in isopropanol. The isoluble oxalate salt is collected and recrystallized from ethanol to give white crystals, mp 152°–154° C., 5,6-dimethoxy-2-methyl-3-[2-(4-phenylhydroxymethyl-piperidyl)-ethyl]indole oxalate.

Analysis:
Calculated for $C_{25}H_{32}N_2O_3 \cdot (CO_2H)_2$: 65.04%C; 6.87%H; 5.62%N.
Found: 65.02%C; 6.87%H; 5.61%N.

EXAMPLE 22

A mixture of 6.2 g of 3-(3-bromopropyl)indole, 5.8 g of 4-(4-fluorobenzoyl)piperidine, free base of Example 10, 3.8 g of potassium carbonate in 65 ml of dimethylformamide is stirred under nitrogen at 50° C for 16 hours. The mixture is stirred while being allowed to cool to ambient temperature and then 180 ml of water are added slowly causing a yellow oil to separate. The supernatant aqueous solution is decanted from the oil and the oil is taken up in ether, the ethereal solution is washed with water and dried and the ether removed in vacuo leaving a white solid. The solid is dissolved in absolute ethanol, and HCl gas bubbled into the solution to produce a salt. Addition of ether to the solution causes the salt to precipitate. The salt is recrystallized from isopropanol to give the white solid, mp 211°–213° C of 3-{3-[4-(4-fluorobenzoyl)piperidyl]propyl}indole hydrochloride.

Analysis:
Calculated for $C_{23}H_{25}FNO_2 \cdot HCl$: 68.69%C; 6.54%H; 6.99%H; 8.84%Cl
Found: 68.84%C; 6.60%H; 6.90%H; 8.65%Cl.

EXAMPLE 23

A sample of 3-{3-[4-(4-fluorobenzoyl)piperidyl]-propyl}indole, free base of Example 22, is reduced and treated by the method described in Example 2 to give 3-{3-[4-(4-fluorophenylhydroxymethyl)piperidyl]-propyl}indole.

EXAMPLE 24

A sample of 3-(3-bromopropyl)-6-methoxy-2-methylindole and 4-(3-fluorobenzoyl)piperidine are treated according to the method described in Example 1e to give 6-methoxy-2-methyl-3-{3-[4-(4-fluorobenzoyl)piperidyl]-propyl}indole hydrochloride.

EXAMPLE 25

A sample of 6-methoxy-2-methyl-3-{3-[4-(4-fluorobenzoyl)piperidyl]propyl}indole, free base of Example 24, is reduced and treated by the method described in Example 2 to give 6-methoxy-2-methyl-3-{3-[4-(4-fluorophenylhydroxymethyl)piperidyl]propyl}indole.

We claim:

1. A method of alleviating pain which comprises adminsitering to a patient an amount pharmaceutically effective for relieving pain of a compound of the formula

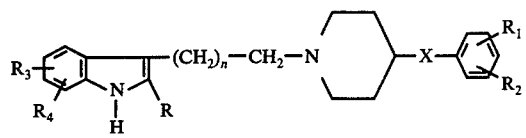

wherein X is

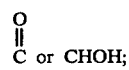

R is hydrogen or methyl; $R_1$ and $R_2$ are the same or different and stand for hydrogen, halogen, straight or branched chain alkyl of up to 5 carbon atoms, alkoxy of up to 5 carbon atoms, trifluoromethyl, hydroxy, phenoxy or phenyl; $R_3$ and $R_4$ are hydrogen or methoxy; $n$ is the integer 1 or 2, or an acid addition salt thereof prepared from a pharmaceutically acceptable acid.

* * * * *

UNITED STATES PATENT AND TRADEMARK OFFICE
CERTIFICATE OF CORRECTION

PATENT NO. : 4,110,459

DATED : August 29, 1978

INVENTOR(S) : Helsley et al.

It is certified that error appears in the above-identified patent and that said Letters Patent are hereby corrected as shown below:

Column 1, line 16, "U.s." should be --U.S.--;

Column 1, line 61, Column 7, lines 22 to 23, Column 8, lines 30 to 31, Column 9, lines 17 and 18, Column 10, lines 65 to 66 and Column 15, line 50, In each instance "...benzoyl)-piperidine" should be
--...benzoyl)piperidine--;

Column 2, line 42, "3-(2-bromo..." should be --3-(ω-bromo...--;

Column 2, line 60 and Column 3, line 5, In the structural formula, the portion

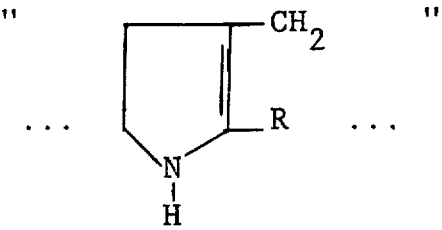

should be

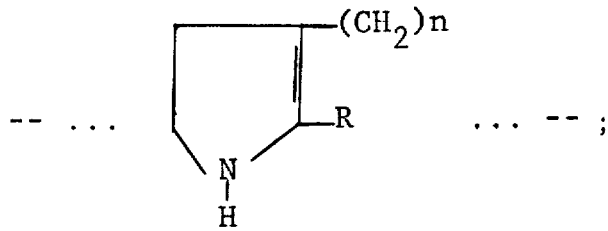

UNITED STATES PATENT AND TRADEMARK OFFICE
CERTIFICATE OF CORRECTION

PATENT NO. : 4,110,459
DATED : August 29, 1978
INVENTOR(S) : Helsley et al.

It is certified that error appears in the above-identified patent and that said Letters Patent are hereby corrected as shown below:

Column 3, line 29, "...benzoyl-1(indol-..." should be --...benzoyl-1-(indol-...--;

Column 3, line 35, In the structural formula, the portion

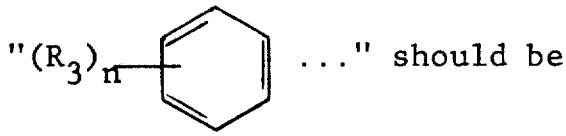 "..." should be

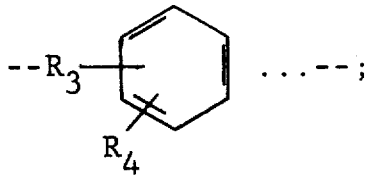 ...--;

Column 3, line 42, After "Step B" insert --in which n is 1--;

Column 3, line 44, "utilized" should be --utilizes--;

Column 3, line 53, "...piperidyl]-ethyl..." should be --...piperidyl]propyl...--;

Column 3, line 55, "10 mg/kg" should be --1 mg/kg--;

Column 3, line 60, In the Table, please insert the following compound and MED:

--3-{2-[4-(4-fluorobenzoyl)piperidyl]ethyl}indole    10--;

UNITED STATES PATENT AND TRADEMARK OFFICE
CERTIFICATE OF CORRECTION

PATENT NO. : 4,110,459

DATED : August 29, 1978

INVENTOR(S) : Helsley et al.

It is certified that error appears in the above-identified patent and that said Letters Patent are hereby corrected as shown below:

Column 4, line 22, Between "doses of" and "11," insert --4.4,--;

Column 4, line 23, After "body weight," insert --3-{3-[4-(4-fluorobenzoyl)piperidyl]propyl}indole hydrochloride,--

Column 4, line 28, "505" should be --50%--;

Column 4, line 45, Delete "and";

Column 4, line 47, Replace the period with a semi-colon (;);

Column 4, between lines 47 and 48, Insert the following:
--5-methoxy-3-{3 [4-(3-methoxybenzol)piperidyl]propyl}indole; and 5,6-dimethoxy-2-methyl-3-{3-[4-trifluoromethylphenylhydroxymethyl)piperidyl]propyl} indole.--;

Column 4, line 49, "resent" should be --present--;

Column 4, line 63, Between "active" and "in" insert --compound--;

Column 5, line 11, "a s" should be --as--;

UNITED STATES PATENT AND TRADEMARK OFFICE
CERTIFICATE OF CORRECTION

PATENT NO. : 4,110,459

DATED : August 29, 1978

INVENTOR(S) : Helsley et al.

It is certified that error appears in the above-identified patent and that said Letters Patent are hereby corrected as shown below:

| | |
|---|---|
| Column 5, line 15, | "a" should be --A--; |
| Column 5, line 23, | "of" should be --or--; |
| Column 5, line 35, | "sythetic" should be --synthetic--; |
| Column 5, line 42, | "dispasable" should be --disposable--; |
| Column 6, line 8, | "withether" should be --with ether--; |
| Column 6, line 57, | "4(3-trifluoro..." should be --4-(3-trifluoro...--; |
| Column 7, line 4, | "resence" should be --presence--; |
| Column 7, line 9, | "0: 74,96%" should be --74.96%C--; |
| Column 7, line 62, | "toluenecyclohexane" should be --toluene-cyclohexane--; |
| Column 8, line 16, Column 15, lines 19 and 55 and Column 16 line 40, | "...piperidyl]-ethyl..." should be --...piperidyl]ethyl...--; |
| Column 9, line 11, | After "48%" delete --of--; |
| Column 9, line 47, | "[145°-147°C., of 3-]2..." should be --145°-147°C., of 3-[2--; |

UNITED STATES PATENT AND TRADEMARK OFFICE
CERTIFICATE OF CORRECTION

PATENT NO. : 4,110,459  
DATED : August 29, 1978  
INVENTOR(S) : Helsley et al.

It is certified that error appears in the above-identified patent and that said Letters Patent are hereby corrected as shown below:

Column 10, line 59, "hours" should be --hour--;

Column 11, line 18, "analysis" should be --Analysis--;

Column 11, line 36, "...methoxy-benzoyl)..." should be --...methoxybenzoyl)...--;

Column 11, line 52, "the" should be --The--;

Column 11, line 52, "ith" should be --with--;

Column 11, line 64, "1(bare" should be --1(b) are--;

Column 12, line 18, "$C_{14}H_{19}NO_{03}\cdot HCl$:" should be --$C_{14}H_{19}NO_3 \cdot HCl$:--;

Column 12, line 18, "58.85%C" should be --58.84%C--;

Column 12, line 19, "4.9%N" should be --4.90%N--;

Column 12, line 37, "73,44%C" should be --73.44%C--;

Column 12, lines 46-47, "manintaining" should be --maintaining--;

Column 14, line 6, "Theoil" should be --The oil--;

Column 14, line 8, Delete "the oil" and insert --to--;

UNITED STATES PATENT AND TRADEMARK OFFICE
CERTIFICATE OF CORRECTION

PATENT NO. : 4,110,459
DATED : August 29, 1978
INVENTOR(S) : Helsley et al.

It is certified that error appears in the above-identified patent and that said Letters Patent are hereby corrected as shown below:

Column 14, line 15, "4(2-" should be --4-(2- --;

Column 14, line 29, "minumum" should be --minimum-- and "ehtanol" should be --ethanol--;

Column 14, line 32, "ethanolether" should be --ethanol-ether--;

Column 14, line 33, "4°(2-..." should be --4-(2-...--;

Column 14, line 40, "dimethyl formamide" should be --dimethylformamide--;

Column 14, line 53, "$C_{22}H_{23}FN_2:O$" should be --$C_{22}H_{23}FN_2O:$--;

Column 15, line 12, "apears" should be --appears--;

UNITED STATES PATENT AND TRADEMARK OFFICE
CERTIFICATE OF CORRECTION

PATENT NO. : 4,110,459

DATED : August 29, 1978

INVENTOR(S) : Helsley et al.

It is certified that error appears in the above-identified patent and that said Letters Patent are hereby corrected as shown below:

Column 16, line 49, "10" should be --1(d)--;

Column 16, line 67, "6.99%H" should be --6.99%N--;

Column 16, line 68, "6.90%H" should be --6.90%N--;

Column 17, line 14, "...piperidyl]-propyl..." should be --...piperidyl]propyl...--.

Signed and Sealed this

Sixth Day of November 1979

[SEAL]

Attest:

RUTH C. MASON
Attesting Officer

LUTRELLE F. PARKER
Acting Commissioner of Patents and Trademarks